(12) United States Patent
Sugiura et al.

(10) Patent No.: US 9,166,081 B2
(45) Date of Patent: Oct. 20, 2015

(54) OPTICAL SENSOR

(71) Applicant: DENSO CORPORATION, Kariya, Aichi-pref. (JP)

(72) Inventors: Makiko Sugiura, Hekinan (JP); Takahiko Yoshida, Okazaki (JP); Kiyoshi Otsuka, Kariya (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 14/406,541

(22) PCT Filed: Sep. 5, 2013

(86) PCT No.: PCT/JP2013/005270
§ 371 (c)(1),
(2) Date: Dec. 9, 2014

(87) PCT Pub. No.: WO2014/038206
PCT Pub. Date: Mar. 13, 2014

(65) Prior Publication Data
US 2015/0179830 A1    Jun. 25, 2015

(30) Foreign Application Priority Data
Sep. 7, 2012  (JP) ................................. 2012-197339

(51) Int. Cl.
*H01L 31/00* (2006.01)
*H01L 31/0232* (2014.01)
(Continued)

(52) U.S. Cl.
CPC ......... *H01L 31/02327* (2013.01); *G01J 1/0209* (2013.01); *G01J 1/0271* (2013.01); *G01J 1/0407* (2013.01); *G01J 1/0437* (2013.01);
(Continued)

(58) Field of Classification Search
CPC ............ H01L 31/02327; H01L 31/101; H01L 31/1013

USPC .............................. 257/80, 82, 432, 435, 440
See application file for complete search history.

(56) References Cited

U.S. PATENT DOCUMENTS 5,811,793 A    9/1998  Pientka
2007/0262239 A1   11/2007  Niigaki et al.
(Continued)

FOREIGN PATENT DOCUMENTS

JP    H6-177416 A    6/1994
JP    2004-198214 A    7/2004
(Continued)

OTHER PUBLICATIONS

International Search Report mailed Dec. 17, 2013 in the corresponding PCT application No. PCT/JP2013/005270 (with English translation).

(Continued)

*Primary Examiner* — Minh-Loan Tran
(74) *Attorney, Agent, or Firm* — Posz Law Group, PLC

(57) ABSTRACT

An optical sensor includes a light receiving portion, a definition portion, and a selection portion. The definition portion defines an incident angle of an incident light that enters the light receiving portion. The selection portion selects a wavelength of the incident light that enters the light receiving portion. The definition portion has a light shielding film disposed above the light receiving portion, and an opening formed in the light shielding film. The selection portion has a slit formed in the light shielding film disposed within a region surrounded by the opening.

5 Claims, 3 Drawing Sheets

(51) Int. Cl.
*G01J 1/06* (2006.01)
*G02B 5/20* (2006.01)
*G01N 21/552* (2014.01)
*G01J 1/02* (2006.01)
*G01J 1/04* (2006.01)
*G01J 1/42* (2006.01)
*H01L 31/0216* (2014.01)
*G01W 1/14* (2006.01)
*H01L 31/09* (2006.01)
*H01L 31/101* (2006.01)
*H01L 31/12* (2006.01)
*B60S 1/08* (2006.01)

(52) U.S. Cl.
CPC ............ *G01J 1/0462* (2013.01); *G01J 1/0488* (2013.01); *G01J 1/06* (2013.01); *G01J 1/4228* (2013.01); *G01N 21/552* (2013.01); *G01W 1/14* (2013.01); *G02B 5/201* (2013.01); *H01L 31/02161* (2013.01); *H01L 31/02325* (2013.01); *H01L 31/09* (2013.01); *H01L 31/101* (2013.01); *H01L 31/12* (2013.01); *B60S 1/0833* (2013.01)

(56) References Cited

U.S. PATENT DOCUMENTS

| | | |
|---|---|---|
| 2009/0008735 A1 | 1/2009 | Ogino et al. |
| 2010/0201834 A1* | 8/2010 | Maruyama et al. ........ 348/222.1 |
| 2010/0220377 A1 | 9/2010 | Yamada et al. |
| 2011/0220976 A1 | 9/2011 | Iida et al. |
| 2012/0075688 A1 | 3/2012 | Yamada et al. |
| 2012/0262606 A1* | 10/2012 | Yagyu .......................... 348/239 |
| 2013/0037700 A1 | 2/2013 | Michiyama et al. |
| 2013/0037902 A1* | 2/2013 | Nakazawa et al. ............ 257/432 |

FOREIGN PATENT DOCUMENTS

| | | |
|---|---|---|
| JP | 2011-203247 A | 10/2011 |
| WO | 2013/015117 A1 | 1/2013 |

OTHER PUBLICATIONS

Written Opinion of the International Searching Authority mailed Dec. 17, 2013 in the corresponding PCT application No. PCT/JP2013/005270 (with English translation).

\* cited by examiner

OPTICAL SENSOR

CROSS REFERENCE TO RELATED APPLICATIONS

The present disclosure is a U.S. national stage application of PCT/JP2013/005270 filed on Sep. 5, 2013, and is based on Japanese Patent Application No. 2012-197339 filed on Sep. 7, 2012, the contents of which are incorporated herein by reference.

TECHNICAL FIELD

The present disclosure relates to an optical sensor including a light receiving portion, a definition portion that defines an incident angle of an incident light that enters the light receiving portion, and a selection portion that selects a wavelength of the incident light.

BACKGROUND ART

Up to now, for example, as disclosed in Patent Literature 1, an optical sensor has been proposed which includes a photodiode, an angle limiting filter that limits an incident angle of an incident light to a light receiving region of the photodiode, and an optical bandpass filter that transmits light of a specific wavelength of the incident light. The angle limiting filter is made of a light shielding material, and the optical bandpass filter is formed of a multilayer thin film. The angle limiting filter is formed on the photodiode, and the optical bandpass filter is formed on the angle limiting filter.

PRIOR ART LITERATURES

Patent Literature

Patent Literature 1 : JP 2011-203247A

SUMMARY OF INVENTION

In the optical sensor disclosed in Patent Literature 1, the angle limiting filter is made of the light shielding material, and the optical bandpass filter is formed of the multilayer thin film. Since the angle limiting filter and the light bandpass filter are separated from each other, a size of the optical sensor increases.

The present disclosure aims to provide an optical sensor that suppresses an increase in the size of the optical sensor.

According to an aspect of the present disclosure, an optical sensor includes a light receiving portion, a definition portion that defines an incident angle of an incident light that enters the light receiving portion, and a selection portion that selects a wavelength of the incident light. The definition portion and the selection portion share a light shielding film disposed above the light receiving portion. The definition portion has an opening formed in the light shielding film, and the selection portion has a slit formed in the light shielding film disposed within a region surrounded by the opening.

According to the present disclosure, an increase in the size of the optical sensor is suppressed as compared with a configuration in which a definition portion and a selection portion are separated from each other.

DESCRIPTION OF EMBODIMENTS

Hereinafter, an embodiment will be described with reference to the drawings, in which the present disclosure is applied to a front windshield of a vehicle. The front windshield corresponds to a transparent plate. An optical sensor according to the present embodiment will be described with reference to FIGS. 1 to 3.

Figure 1:
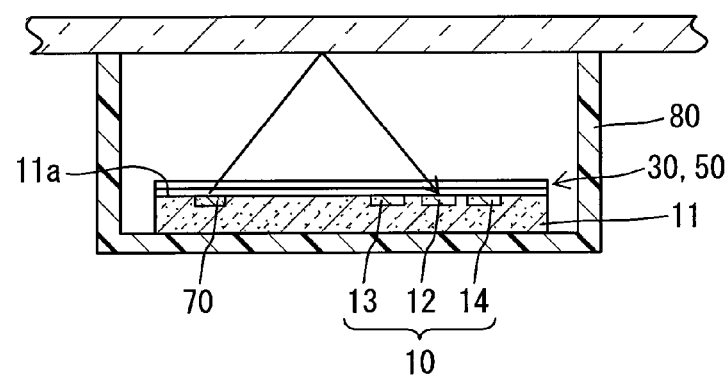
FIG. 1 is a cross-sectional view illustrating a schematic configuration of an optical sensor according to an embodiment.

An optical sensor 100 includes a light receiving portion 10, a definition portion 30, and a selection portion 50. The definition portion 30 defines an incident angle of an incident light that is input to the light receiving portion 10, and the selection portion 50 selects a wavelength of the incident light. The optical sensor 100 includes a light emitting portion 70 and a housing portion 80 in addition to the light receiving portion 10, the definition portion 30, and the selection portion 50. As illustrated in FIG. 1, the housing portion 80 is mounted on an inner wall surface of the front windshield, and the light receiving portion 10, the definition portion 30, the selection portion 50, and the light emitting portion 70 are disposed within a housing space formed by the housing portion 80 and the front windshield. An exterior light through the front windshield, the definition portion 30, and the selection portion 50, and a light emitted from the light emitting portion 70 are incident to the light receiving portion 10.

The light receiving portion 10 converts an incident light having the incident angle defined by the definition portion 30 and the wavelength selected by the selection portion 50 into an electric signal. The light receiving portion 10 is formed of a photodiode having a PN junction, and formed on a formation surface 11a of a semiconductor substrate 11. The light receiving portion 10 has three light receiving portions 12 to 14, and light receiving ranges (wavelength bandwidths of detectable light) of the respective light receiving portions 12 to 14 are different from each other.

Figure 2:
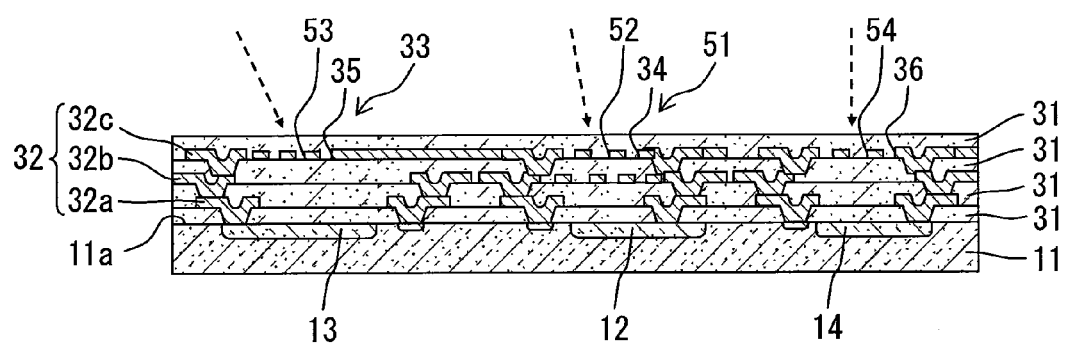
FIG. 2 is a cross-sectional view illustrating a main portion of the optical sensor.

The definition portion 30 includes a transparent film 31 having a translucency, a light shielding film 32 having a light shielding property, and an opening 33 formed in the light shielding film 32. As illustrated in FIG. 2, the light shielding film 32 includes a first film 32a, a second film 32b, and a third film 32c, which are stacked at predetermined intervals above the formation surface 11a (light receiving portion 10) in the stated order. The opening 33 includes openings 34 to 36 corresponding to the respective light receiving portions 12 to 14, and as indicated by dashed arrows in FIG. 2, the incident angles of the incident lights defined by the openings 34 to 36 are different from each other. Further, as indicated by dashed lines in FIG. 3, opening areas of the respective openings 34 to 36 are different from each other.

The selection portion 50 shares the light shielding film 32 with the definition portion 30, and has a slit 51 formed in the shared light shielding film 32. As described above, the first film 32a, the second film 32b, and the third film 32c are stacked at the predetermined intervals above the formation surface 11a. The selection portion 50 shares the second film 32b and the third film 32c away from the formation surface 11a in the light shielding film 32 with the definition portion 30, and the slit 51 is formed in the shared second film 32b and third film 32c.

The slit 51 includes slits 52 to 54 which are located in a region surrounded by the opening 33, and which correspond to the respective light receiving portions 12 to 14. The wavelengths of the incident lights selected by the slits 52 to 54 are different from each other. The first slit 52 selects a wavelength bandwidth mainly included in the light emitted by the light emitting portion 70, and the second slit 53 selects a wavelength bandwidth except for the wavelength bandwidth mainly included in the light emitted by the light emitting portion 70. The third slit 54 selects infrared rays. As illustrated in FIG. 2, the first slit 52 is formed in each of the second film 32b and the third film 32c, and the slit 53, 54 is formed in the third film 32c.

Figure 3:
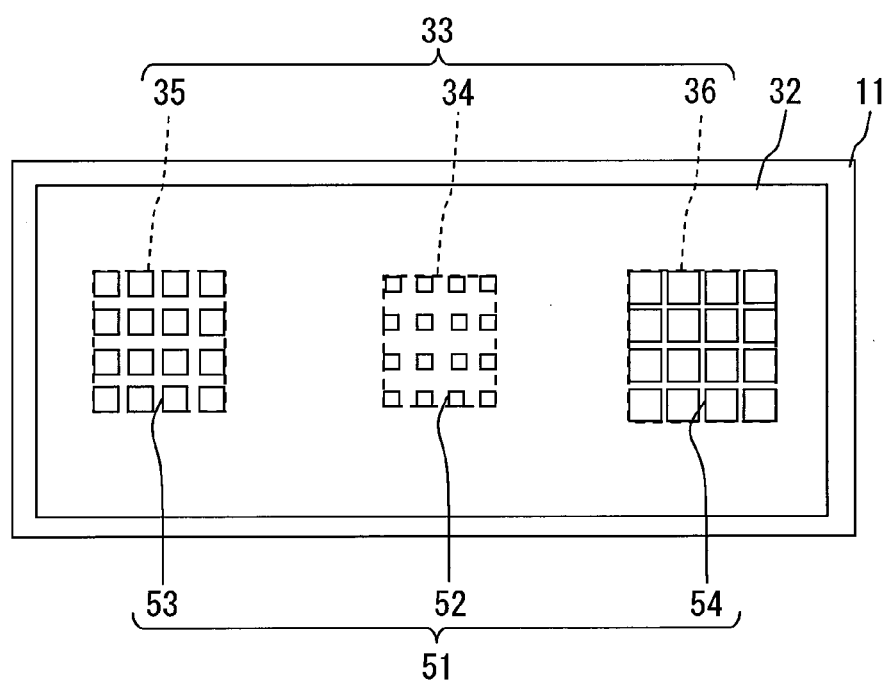
FIG. 3 is a top view illustrating openings and slits.

As illustrated in FIG. 3, the slits 52 to 54 are formed in the light shielding film 32 in the region surrounded by the opening 33, and planar shapes of the slits 52 to 54 are rectangular. A filter using a surface plasmon resonance is formed by the plural slits 51, and the wavelength of the incident light to be selected is determined according to the filter.

The surface plasmon is present on an interface of two different materials. When a light having an energy which resonates with the surface plasmon, that is, a light having a wavelength bandwidth which is resonant is incident on the interface, the light resonates with the surface plasmons, and the intensity of light increases. As a result, the light having the increased intensity is made incident to the light receiving portion 10. The surface plasmons depend on the physical properties and the shape of the two materials forming the interface, and an interval between the respective interfaces. For that reason, the light of the wavelength bandwidth the intensity of which increases can be selected with an appropriate change in the material forming the interface, an appropriate change in the shape of the interface, and an appropriate change in the interval between the respective interfaces. According to the present embodiment, the light of the wavelength bandwidth the intensity of which increases can be selected with an appropriate change in the material forming the transparent film 31 and the light shielding film 32, an appropriate change in the shape of the slit 51, and an appropriate change in the interval of the slits 51.

The light emitting portion 70 emits light to the front windshield, and makes a reflected light reflected by the front windshield incident to the first light receiving portion 12. The light emitting portion 70 according to the present embodiment is formed of an LED, and the wavelength bandwidth of the emitted light is longer in wavelength than a visible light. The light emitting portion 70 is disposed on the semiconductor substrate 11, but may not be disposed on the same semiconductor substrate 11 as that of the light receiving portion 10. The light emitting portion 70 may be disposed on another substrate different from that of the light receiving portion 10.

The housing portion 80 determines a relative position of the light receiving portion 10 and the front windshield while housing the light receiving portion 10, the definition portion 30, the selection portion 50, and the light emitting portion 70. The housing portion 80 is made of a material that absorbs light emitted from the light emitting portion 70.

Subsequently, various sensors formed by the optical sensor 100 will be described. As described above, the light receiving portion 10 includes the three light receiving portions 12 to 14, the opening 33 of the definition portion 30 includes the three openings 34 to 36, and the slit 51 of the selection portion 50 includes the three slits 52 to 54. The first light receiving portion 12, the first opening 34, the first slit 52, and the light-emitting portion 70) configure a rain sensor for detecting rainfall, and the second light receiving portion 13, the second opening 35, and the second slit 53 configure an angle sensor for detecting the incident angle of light incident on the vehicle. The third light receiving portion 14, the third opening 36, and the third slit 54 configure a solar radiation sensor for detecting the amount of solar radiation. In addition, the first light receiving portion 12 corresponds to a rain sensor light receiving portion, the second light receiving portion 13 corresponds to an angle sensor light receiving portion, and the third light receiving portion 14 corresponds to a solar radiation sensor light receiving portion.

The advantageous effects of the optical sensor 100 according to the embodiment will be described. As described above, the definition portion 30 and the selection portion 50 share the light shielding film 32 with each other. The definition portion 30 has the opening 33 formed in the light shielding film 32, and the selection portion 50 has the slits 51 formed of the light shielding film 32. According to this configuration, an increase in the size of the optical sensor 100 is suppressed as compared with the configuration in which the definition portion and the selection portion are separated from each other.

The wavelengths of the incident lights selected by the slits 52 to 54 are different from each other. According to this configuration, the lights different in the wavelength can be detected by the light receiving portions 12 to 14.

The first slit 52 corresponding to the first light receiving portion 12 selects a wavelength bandwidth mainly included in the light emitted by the light emitting portion 70. According to the above configuration, the light having a wavelength bandwidth except for the wavelength bandwidth mainly included in the light emitted by the light emitting portion 70 is prevented from entering the first light receiving portion 12. For that reason, the incidence of ambient light to the first light receiving portion 12 is suppressed, and a reduction in the detection accuracy of the rainfall is suppressed.

The second slit 53 corresponding to the second light receiving portion 13 selects a wavelength bandwidth except for the wavelength bandwidth mainly included in the light emitted by the light emitting portion 70. According to the above configuration, the light emitted by the light emitting portion 70 is prevented from entering the second light receiving portion 13. For that reason, a reduction in the detection accuracy of the incident angle of light is suppressed.

The third slit 54 corresponding to the third light receiving portion 14 selects infrared rays. The infrared radiation has the effect of giving heat to an object. Therefore, a temperature rise of the optical sensor 100 by the radiation can be detected by detection of the infrared rays by the third light receiving portion 14.

The first film 32a, the second film 32b, and the third film 32c are stacked above the formation surface 11a, and the openings 33 are formed in each of the first film 32a, the second film 32b, and the third film 32c. According to the above configuration, one light shielding film is stacked above the formation surface, and the incident angle can be narrowed as compared to the configuration in which the opening is formed in the light shielding film.

The definition portion 30 and the selection portion 50 share the second film 32b and the third film 32c with each other, and the first slit 52 corresponding to the first light receiving portion 12 is formed in the second film 32b and the third film 32c. According to the above configuration, as compared to the configuration in which the first slit is formed in one light shielding film, a half-value width of the incident light incident to the first light receiving portion 12 is narrowed, and the entrance of ambient light into the first light receiving portion 12 is suppressed. For that reason, a reduction in the detection accuracy of rainfall is suppressed. Incidentally, the half-value width is a width from a peak value to a half value of the peak value, of the intensity of incident light.

The incident angles of the incident lights defined by the openings 34 to 36 corresponding to the respective light receiving portions 12 to 14 are different from each other. According to the above configuration, the lights different in the incident angle can be detected by the respective light receiving portions 12 to 14.

The preferred embodiment of the present disclosure has been described above. However, the present disclosure is not limited to the embodiment described above, and various modifications can be implemented without departing from the spirit of the present disclosure.

In this embodiment, an example in which a planar shape of the slit 51 is rectangular is described. However, the planar shape of the slit 51 is not limited to the above example, but may employ, for example, a circle, an ellipse, or a polygon.

Figure 4:
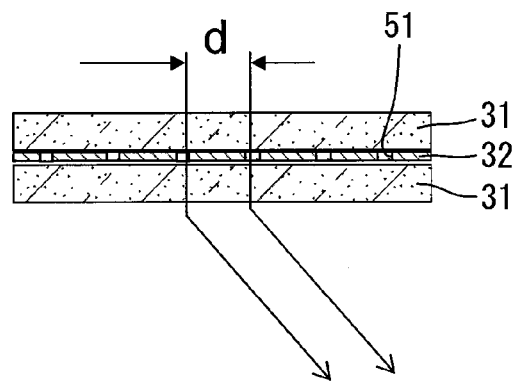
FIG. 4 is a cross-sectional view illustrating one modification of the slits.
Figure 5:
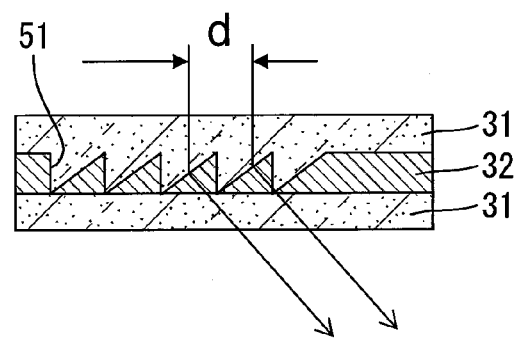
FIG. 5 is a cross-sectional view illustrating another modification of the slits.
Figure 6:
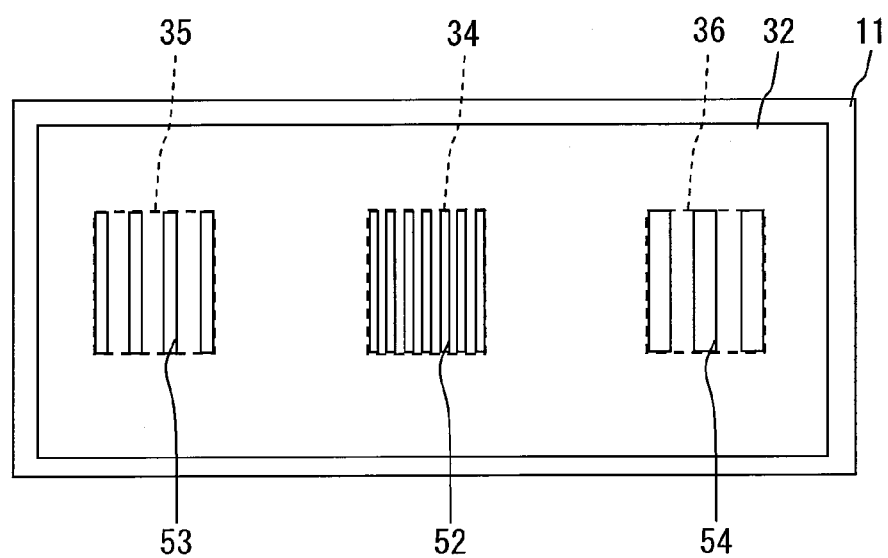
FIG. 6 is a top view illustrating still another modification of the slits.

In this embodiment, an example in which the filter using the surface plasmons resonance is formed by the plural slits 51 formed in the light shielding film 32 in the region surrounded by the opening 33, is described. However, the filter formed by the slits 51 is not limited to the above example. For example, as illustrated in FIGS. 4 to 6, filters using a diffraction grating can be formed by the slits 51.

When a light is made incident to the diffraction grating, the light is diffracted by the slits 51 constituting the diffraction grating. The lights diffracted by the respective slits 51 interfere with each other to increase the intensity of light having a specific wavelength. As a result, the light having the increased intensity is made incident to the light receiving portion 10. In addition, the specific wavelength at which the intensity increases depends on a width d of the slit 51, and the shape of the slit 51. For that reason, the light of the wavelength bandwidth the intensity of which increases can be selected with an appropriate change in the width d of the slit 51, and an appropriate change in the shape of the slit 51.

In this embodiment, an example in which the first film 32a, the second film 32b, and the third film 32c are stacked at the predetermined intervals above the formation surface 11a is described. However, the light shielding film 32 stacked above the formation surface 11a is not limited to the above example. For example, the number of light shielding films 32 may be one, two, or four.

In this embodiment, an example in which the selection portion 50 shares the second layer 32b and the third layer 32c away from the formation surface 11a in the three light shielding films 32 with the definition portion 30 is described. However, the number of films to be shared is not limited to the above example, but may be any number as long as one or more films are provided.

In this embodiment, an example in which the wavelengths of the incident lights selected by the slits 52 to 54 are different from each other is described. However, the wavelengths of the incident lights selected by the slits 52 to 54 may not be different from each other.

In this embodiment, an example in which the first slit 52 is formed in each of the second film 32b and the third film 32c, and the slit 53, 54 is formed in the third film 32c is described. However, the slits 52 to 54 may be formed in at least one of the plural light shielding films 32 shared by the selection portion 50 with the definition portion 30.

In this embodiment, an example in which the incident angles of the incident lights defined by the openings 34 to 36 are different from each other is described. However, the incident angles of the incident lights defined by the openings 34 to 36 may not be different from each other.

In this embodiment, an example in which the respective opening areas of the openings 34 to 36 are different from each other is described. However, the respective opening areas of the openings 34 to 36 may not be different from each other.

In this embodiment, an example in which the light receiving portion 10 has the light receiving portions 12 to 14 is described. However, the number of light receiving portions is not limited to the above example.

In this embodiment, an example in which a rain sensor, an angle sensor, and a solar radiation sensor are each configured by the optical sensor 100 is described. However, the sensors configured by the optical sensor 100 are not limited to the above example. Also, the number of configured sensors is not limited to the above example.

The invention claimed is:

1. An optical sensor comprising:
a light receiving portion;
a light emitting portion that emits a light to a transparent plate;
a definition portion that defines an incident angle of an incident light that enters the light receiving portion; and
a selection portion that selects a wavelength of the incident light, wherein
the definition portion and the selection portion share a light shielding film disposed above the light receiving portion with each other,
the definition portion has an opening formed in the light shielding film,
the selection portion has a slit formed in the light shielding film disposed within a region surrounded by the opening,
the light receiving portion has a plurality of light receiving portions,
the slit has a plurality of slits corresponding to the plurality of light receiving portions, respectively,
wavelengths of incident lights selected by the plurality of slits are different from each other,
one of the plurality of light receiving portions is a rain sensor light receiving portion applied to a rain sensor that detects rainfall, in which a reflected light reflected by the transparent plate is incident,
the slit corresponding to the rain sensor light receiving portion selects a wavelength bandwidth mainly included in light emitted by the light emitting portion,
one of the plurality of light receiving portions is an angle sensor light receiving portion applied to an angle sensor that detects an incident angle of light, and
the slit corresponding to the angle sensor light receiving portion selects a wavelength bandwidth except for a wavelength bandwidth mainly included in light emitted by the light emitting portion.

2. The optical sensor according to claim 1, wherein
one of the plurality of light receiving portions is a solar radiation sensor light receiving portion applied to a solar radiation sensor that detects an amount of solar radiation, and
the slit corresponding to the solar radiation sensor light receiving portion selects infrared rays.

3. The optical sensor according to claim 1, wherein
the light shielding film includes a plurality of films stacked at predetermined intervals above the light receiving portion,
the definition portion and the selection portion share at least one of the plurality of films with each other,
the opening is formed in each of the plurality of films, and the slit is formed in the at least one of the plurality of films shared by the definition portion and the selection portion.

4. The optical sensor according to claim 3, wherein
the definition portion and the selection portion share at least two of the plurality of films with each other, and
the slit corresponding to the rain sensor light receiving portion is formed in the at least two of the plurality of films shared by the definition portion and the selection portion.

5. The optical sensor according to claim 1, wherein
the opening has a plurality of openings corresponding to the plurality of light receiving portions, respectively, and
incident angles of incident lights defined by the plurality of openings are different from each other.

* * * * *